(12) United States Patent
Maase et al.

(10) Patent No.: US 7,858,802 B2
(45) Date of Patent: Dec. 28, 2010

(54) METHOD OF PREPARING IONIC LIQUIDS

(75) Inventors: Matthias Maase, Speyer (DE); Klemens Massonne, Bad Dürkheim (DE); Laszlo Szarvas, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 777 days.

(21) Appl. No.: 10/587,248

(22) PCT Filed: Jan. 26, 2005

(86) PCT No.: PCT/EP2005/000752

§ 371 (c)(1),
(2), (4) Date: Jul. 26, 2006

(87) PCT Pub. No.: WO2005/070896

PCT Pub. Date: Aug. 4, 2005

(65) Prior Publication Data

US 2007/0142646 A1    Jun. 21, 2007

(30) Foreign Application Priority Data

Jan. 26, 2004    (DE)    ........................ 10 2004 003 958

(51) Int. Cl.
C07D 233/58    (2006.01)
C25B 9/10    (2006.01)
H01G 9/02    (2006.01)

(52) U.S. Cl. ........................ 548/110; 204/242; 252/62.2
(58) Field of Classification Search ................. 548/110; 204/242; 252/62.2
See application file for complete search history.

(56) References Cited

U.S. PATENT DOCUMENTS

| | | |
|---|---|---|
| 2004/0073035 A1 | 4/2004 | Maase et al. |
| 2004/0133058 A1 | 7/2004 | Arlt et al. |
| 2005/0020857 A1 | 1/2005 | Volland et al. |

FOREIGN PATENT DOCUMENTS

| | | |
|---|---|---|
| DE | 102 02 838 A1 | 8/2003 |
| EP | 0 291 074 A2 | 11/1988 |
| EP | 0 291 074 A3 | 11/1988 |
| EP | 1 182 196 A1 | 2/2002 |
| EP | 1 182 197 A1 | 2/2002 |
| WO | WO 98/47618 * | 10/1998 |
| WO | WO-01/40146 A1 | 6/2001 |
| WO | WO-01/77081 A1 | 10/2001 |
| WO | WO-02/074718 A2 | 9/2002 |
| WO | WO-02/074718 A3 | 9/2002 |
| WO | WO-2004/005222 A2 | 1/2004 |
| WO | WO-2004/005222 A3 | 1/2004 |
| WO | WO-2005/019183 A1 | 3/2005 |

OTHER PUBLICATIONS

Xu, Wu and Angell, Austen, "Novel Orthoborate Ionic Liquids," Dept. of Chem., Arizona State University, Presented at 202nd Meeting of the Electrochemical Society, Oct. 20-25, 2002, Salt Lake City, Utah.*
Wasserscheid and Keim, Angew. Chem. Int. Ed., 2000, 39, 3772-3789.*
"Ionic Liquids in Synthesis" Wasserscheid et al., *Wiley-VCH*, 2, 2003, Chapter 2, Davis, Jr et al., Synthesis and Purification of Ionic Liquids, pp. 7-17.
"Novel Ionic Liquid Thermal Storage for Solar Thermal Electric Power Systems", Wu et al., *Solar Energy: The Power to Choose*, Proceedings of Solar Forum Apr. 21-25, 2001, 7 pages.
"Room termperature ionic liquids as novel media for 'clean' liquid-liquid extraction" Huddleston et al., *Chem. Commun.* 1998, pp. 1765-1766.
"Transition Metal Catalysed Reactions in Room-Temperature Ionic Liquids" Dyson et al., *Electrochemical Society Proceedings*, vol. 99-41, 2000, pp. 161-168.
"Air and Water Stable 1-Ethyl-3-methylimidazolium Based Ionic Liquids" Wilkes et al., *J. Chem. Soc., Chem. Commun.*, 1992, pp. 965-967.

* cited by examiner

*Primary Examiner*—Robert Havlin
(74) *Attorney, Agent, or Firm*—Connolly Bove Lodge & Hutz LLP

(57) ABSTRACT

In the process for preparing ionic liquids, an ionic liquid is firstly reacted with an alkoxide or with barium hydroxide and is subsequently neutralized with an acid. The ionic liquid contains a phosphonium and/or ammonium cation and an anion selected from the group consisting of halides, arylsulfonates, alkylsulfonates, sulfate, hydroxysulfate, alkylsulfates, hydrogencarbonate, carbonate. triflate and carboxylates. In this process, virtually any anions can be introduced into the ionic liquids.

3 Claims, No Drawings

METHOD OF PREPARING IONIC LIQUIDS

This application is a National Stage of PCT/EP2005/000752 filed Jan. 26, 2005 which in turn claims priority from German Application 10 2004 003 958.5 filed Jan. 26, 2004.

The present invention relates to a process for preparing ionic liquids.

Ionic liquids are, according to the definition of Wasserscheid and Keim in: Angewandte Chemie 2000, 112, 3926-3945, salts which have a nonmolecular, ionic character and melt at relatively low temperatures. They are liquid at relatively low temperatures and at the same time have a relatively low viscosity. They have very good solvent capabilities for a large number of organic, inorganic and polymeric substances. Furthermore, they are generally noncombustible, noncorrosive and have no measurable vapor pressure.

Ionic liquids are compounds which are made up of positive and negative ions but are electrically neutral overall. Both the positive and the negative ions are predominantly monovalent, but multivalent anions and/or cations, for example ions having from one to five, preferably from one to four, particularly preferably from one to three and in particular one or two, electrical charges per ion are also possible. The charges can be located in various localized or delocalized regions within the molecule, i.e. in a betaine-like fashion, or can also be present on separate anions and cations. Preference is given to ionic liquids whose compounds are made up of at least one cation and at least one anion.

Known fields of application for ionic liquids are, for example, as solvents for chemical reactions, for example as described in Peter Wasserscheid, Chemie in unserer Zeit, 37 (2003) No. 1, pages 52-63, as auxiliaries for separating acids from chemical reaction mixtures, for example as described in DE 102 02 838, as auxiliaries for extractive rectification for separating close-boiling or azeotropic mixtures, for example as described in WO 02/074718, or as heat transfer media in solar-thermal units, for example as described in Proceedings of Solar Forum, Apr. 21-25, 2001, Washington D.C. The use of ionic liquids as extractants for the separation of substances is also mentioned in J. G. Huddleston et al., Chem. Commun. 1998, pages 1765-1766.

When ionic liquids are used, their purity is of great importance. Impurities in ionic liquids can, for example, have an adverse effect on the course of chemical reactions. Thus, P. Teisen et al. in Electrochemical Society Proceedings, Vol. 99-41, pages 161-168, refer to problems when using chloride-containing ionic liquids in liquid-phase hydrogenation and in the Suzuki reaction catalyzed by transition metals, which problems are attributable to impurities. High demands are therefore made of the purity of the desired liquid in the preparation of ionic liquids.

The synthesis of binary ionic liquids of the type $[A]^+[Y]^-$ can be carried out, for example, by means of a two-stage process (J. S. Wilkes, M. J. Zaworotko, J. Chem. Soc., Chem. Commun., 13, 1992, page 965). Here, the organic ammonium salt $[NR^1R^2R^3R]^+X^-$ or the organic phosphonium salt $[PR^1R^2R^3R]^+X^-$ is firstly formed by reaction of an alkylating agent LX and an amine $NR^1R^2R^3$ or a phosphane $PR^1R^2R^3$ in a quaternization reaction. $X^-$ is generally a halide ion. The organic halide salt is isolated and in a subsequent, second reaction stage reacted with an alkali metal salt or alkaline earth metal salt of the type $M^+[Y]^-$ in an exchange reaction. This occurs in a solvent in which the byproduct $M^+X^-$ formed is sparingly soluble but the ionic liquid $[A]^+[Y]^-$ to be synthesized is readily soluble.

A disadvantage of this synthetic reaction is that quantitative exchange of the halide salt $[NR^1R^2R^3R]^+X^-$ or $[PR^1R^2R^3R]^+X^-$ to form the desired ionic liquid $[NR^1R^2R^3R]^+[Y]^-$ or $[PR^1R^2R^3R]^+[Y]^-$ is only obtained when the reaction system is completely free of water under the exchange conditions. These halide ions can act as catalyst poisons, for example when the ionic liquid is used in reactions catalyzed by transition metals. Furthermore, this process has the disadvantage that the halide salt prepared initially is highly hydroscopic.

EP 1 182 197 describes a process for preparing ionic liquids of the general formula $[A]_n^+[Y]^{n-}$, in which the above-described method is employed and the intermediates are not isolated.

EP 1 182 196 describes a process for preparing ionic liquids of the general formula $[A]_n^+[Y]^{n-}$ by alkylation of the parent amines, phosphines, imidazoles, pyrazoles, triazoles or pyridines by means of a disulfate of the general formula $R'-SO_4-R''$ and subsequent replacement of the sulfate anion $R'-SO_4^-$ or $R''-SO_4^-$ by the anion $[Y]^-$ or $[Y]^{2-}$.

Further synthetic routes to ionic liquids are described in "Ionic Liquids in Synthesis" by Peter Wasserscheid and Tom Welton, 2003, Wiley-VCH, 2003, Chapter 2, pages 7 to 17. These essentially involve the precipitation of halides of ionic liquids with silver salts, which is, however, disadvantageous for economic reasons. The preparation of ionic liquids by ion exchange on a resin is also expensive and can be implemented only with difficulty. In addition, use of ion exchange resins requires regeneration of the resins. Finally, the replacement of halides of ionic liquids by washing with water to modify them, which is likewise known is restricted to hydrophobic ionic liquids which are immiscible with water, but these tend to be the exception.

It is accordingly an object of the present invention to provide a generally applicable process for modifying or preparing ionic liquids, which does not have the disadvantages discussed above and leads to products which can be obtained in high purity and yield as direct process product.

The achievement of this object starts up from a process for modifying ionic liquids containing a phosphonium and/or ammonium cation as cation and an anion selected from the group consisting of halides, arylsulfonates, alkylsulfonates, sulfate, hydrogensulfate, alkylsulfates, hydrogencarbonate, carbonate, triflates and carboxylates. In the process of the invention, these ionic liquids are then reacted with an alkoxide or a hydroxide in a first process step, resulting in strongly basic ionic liquids, and the strongly basic ionic liquids are neutralized with an acid in a second process step.

According to the present invention the wording "modification of ionic liquids" is understood in general as an exchange (substitution) of the anion of the ionic liquid.

The ionic liquid to be modified which is used in the process of the invention is preferably easy to prepare. Suitable ionic liquids therefore preferably have the general formula (I)

where n=1, 2, 3 or 4 and the cation $[Q^+]$ is a phosphonium and/or ammonium cation which is selected from the following group, namely from among quaternary ammonium cations from the general formula

phosphonium cations of the general formula

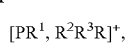

imidazolium cations of the general formula

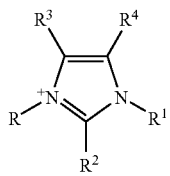

and also all isomeric imidazolinium cations and imidazolidinium cations analogous to this formula, H-pyrazolium cations of the general formula

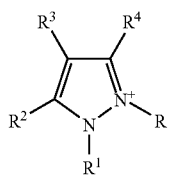

and also 3H-pyrazolium cations, 4H-pyrazolium cations, 1-pyrazolinium cations, 2-pyrazolinium cations and 3-pyrazolinium cations, pyridinium cations of the general formula

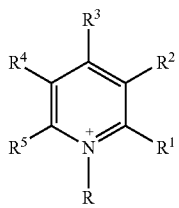

and also pyridazinium, pyrimidinium and pyrazinium cations, pyrrolidinium cations of the general formula

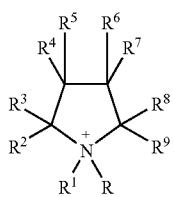

five- to at least six-membered heterocyclic cations which contain at least one phosphorus or nitrogen atom and optionally an oxygen or sulfur atom, for example thiazolium, oxazolium, 1,2,4-triazolium or 1,2,3-triazolium cations; preferably compounds which contain at least one five- or six-membered heterocycle containing one, two or three nitrogen atoms and a sulfur or oxygen atom, particularly preferably compounds containing one or two nitrogen atoms, triazole cations of the general formula

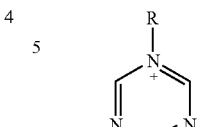

where the triazole ring can be substituted by at least one group selected from the group consisting of $C_1$-$C_6$-alkyl, $C_1$-$C_6$-alkoxy, amino-$C_1$-$C_6$-alkyl, $C_5$-$C_{12}$-aryl or $C_5$-$C_{12}$-aryl-$C_1$-$C_6$-alkyl groups, the 1,8-diazabicyclo[5.4.0]undec-7-enium cation and also the 1,8-diazabicyclo-[4.3.0]non-5-enium cation

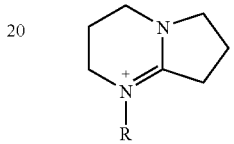

quinolinium cations of the general formula

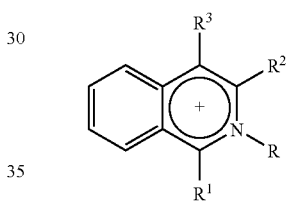

thiazolium cations of the general formula

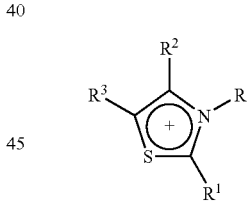

triazinium cations of the general formula

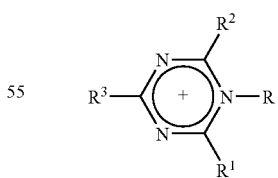

and also oligomers and polymers in which these cations are present, where the radicals R, $R^1$, $R^2$, $R^3$, $R^4$, $R^5$, $R^6$, $R^7$, $R^8$ and $R^9$ are each, independently of one another, hydrogen, $C_1$-$C_{18}$-alkyl, $C_6$-$C_{12}$-aryl, $C_5$-$C_{12}$-cycloalkyl, $C_2$-$C_{18}$-alkyl which may be interrupted by one or more oxygen and/or sulfur atoms and/or one or more substituted or unsubstituted imino groups or a five- or six-membered, oxygen-, nitrogenand/or sulfur-containing heterocycle or two of them together form an unsaturated, saturated or aromatic ring which may be interrupted by one or more oxygen and/or sulfur atoms and/or one or more substituted or unsubstituted imino groups, where each of the radicals mentioned may be substituted by functional groups, aryl, alkyl, aryloxy, alkyloxy, halogen, heteroatoms and/or heterocycles.

The cation present in the ionic liquid to be modified which is used as starting material in the process of the invention is preferably a heterocyclic cation, particularly preferably an imidazolium, pyridinium or phosphonium cation, in particular an imidazonium cation, especially a 1,3-substituted imidazolium cation, for example 1,3-dimethylimidazolium, 1-ethyl-3-methylimidazolium, 1-methyl-3-propylimidazolium, 1-isopropyl-3-methylimidazolium, 1-butyl-3-methylimidazolium, 1-methyl-3-pentylimidazolium, 1-hexyl-3-methylimidazolium, 1-heptyl-3-methylimidazolium, 1-methyl-3-octylimidazolium, 1-decyl-3-methylimidazolium, 1-methyl-3-benzylimidazolium, 1-methyl-3-(3-phenylpropyl)imidazolium, 1-(2-ethyl)hexyl-3-methylimidazolium, 1-methyl-3-nonylimidazolium, 1-methyl-3-decylimidazolium, 1,2,3-trimethylimidazolium, 1-ethyl-2,3-dimethylimidazolium or 1-butyl-2,3-dimethylimidazolium.

The ionic liquids used in the process of the invention contain an anion $[Z]^{n-}$, which is the partly or fully deprotonated anion of an inorganic or organic protic acid $H_nA$, where n is a positive integer and indicates the charge on the anion.

The anion $[Z]^{n-}$ of the ionic liquid to be modified in the process of the invention is selected from the group consisting of halides, arylsulfonates, alkylsulfonates, sulfate, hydrogensulfate, alkylsulfates, hydrogencarbonate, carbonate, alkylcarbonates, triflates and carboxylates. Preference is given to anions $[Z]^{n-}$ which form sparingly soluble salts with the cations of the alkoxides or hydroxides used.

In the first process step of the process of the invention, the above-described ionic liquid to be modified is reacted with a hydroxide, a hydrogencarbonate, a carbonate, a carboxylate or an alkoxide. This forms a strongly basic ionic liquid of the general formula (II)

$$[Q^+]_n[X]^{n-} \tag{II}$$

where $[X]^{n-}=OH^-$, hydrogencarbonates $HCO_3^-$, carbonates $CO_3^{2-}$, carboxylates and alkoxides.

The $pK_s$ of the corresponding acid of the anion of the strongly basic ionic liquid is preferably greater than 1.9, particularly preferably greater than 3, in particular greater than 4, especially greater than 7.

The cations of the hydroxides, hydrogencarbonates, carbonates, carboxylates or alkoxides used are preferably selected so that the salt formed from the cation and the anion $[Z]^{n-}$ in the first process step is sparingly soluble in the solvent used and precipitates. Suitable cations are, for example, alkali metal cations, alkaline earth metal cations and ammonium cations, particularly preferably $Li^+$, $Na^+$, $K^+$, $Rb^+$, $NH_4^+$, $Ca^{2+}$, $Ba^{2+}$ and $Mg^{2+}$, in particular $Li^+$, $Na^+$, $K^+$ and $Ba^{2+}$, especially $K^+$, $Na^+$ and $Ba^{2+}$.

If an alkoxide is used in the first process step of the process of the invention, this alkoxide is preferably selected from the group consisting of alkoxides $RO^-$ where $R=C_1-C_{18}$-alkyl, $C_6-C_{12}$-aryl and $C_5-C_{12}$-cycloalkyl. The alkoxide is particularly preferably selected from the group consisting of tert-butoxide, n-butoxide, isopropoxide, n-propoxide, isobutoxide, ethoxide, methoxide, n-pentoxide, isopentoxide, 2-ethylhexoxide, 2-propylheptoxide, nonoxide, octoxide, decoxide and isomers of the above-mentioned alkoxides. In particular, the alkoxide is selected from the group consisting of tert-butoxide, isopropoxide, ethoxide and methoxide. The alkoxide is especially preferably tert-butoxide or methoxide.

If a carboxylate is used in the first process step of the process of the invention, this carboxylate is preferably selected from the group consisting of acetate, propionate, benzoate, n-butyrate and isobutyrate and pivalate.

If a hydroxide is used in the first process step of the process of the invention, this hydroxide is preferably barium hydroxide.

If the ionic liquid to be modified in the process of the invention is reacted with an alkoxide, this reaction preferably takes place in an alcoholic solvent. Suitable alcoholic solvents are, for example, tert-butanol, isobutanol, isopropanol, ethanol, methanol, n-butanol, n-propanol, n-pentanol, isopentanol, 2-ethylhexanol, 2-propylheptanol, nonanol, octanol, isomer mixtures and mixtures of the abovementioned alcohols. Particular preference is given to tert-butanol, isopropanol, ethanol and methanol. Very particular preference is given to tert-butanol and methanol.

However, the reaction can also be carried out in conventional solvents, for example ethers such as methyl tert-butyl ether, tetrahydrofuran, dioxane or glyme; acetone, acetonitrile, dimethylformamide, dimethyl sulfoxide, chloroform, methylene chloride, diethylacetamide, diethyl ketone, methyl ethyl ketone, dimethylurea or amines such as triethylamine, pyridine or pyrrolidine.

The reaction can also be carried out in mixtures of the abovementioned alcohols and conventional solvents, as long as these are miscible with one another. The reaction in the first process step can also, if appropriate, be carried out directly in the alkoxide or hydroxide, as long as this is liquid.

In a preferred embodiment of the present invention, the acid which is used in the second process step for introducing the desired anion into the ionic liquid is employed as solvent in the first process step. In this embodiment, the addition of the acid in the second process step is preferably omitted.

If the ionic liquid to be modified is reacted with barium hydroxide in the process of the invention, this reaction preferably takes place in water as solvent. However, the above-discussed conventional solvents can also be used, if appropriate in admixture with water.

The use of barium hydroxide is particularly preferred when ionic liquids which contain a sulfate anion or hydrogensulfate anion are used as starting material, since the sparingly soluble $BaSO_4$ is formed. As barium hydroxide, preference is given to using $Ba(OH)_2.8H_2O$.

The reaction of the ionic liquid to be modified in the process of the invention with the alkoxide or the barium hydroxide is carried out at temperatures of preferably from 5 to 100° C., particularly preferably from 10 to 90° C., in particular from 30 to 85° C. The reaction time is preferably from 1 to 16 hours, particularly preferably from 30 minutes to 3 hours, in particular from 10 minutes to 2 hours. Since barium hydroxide is only moderately soluble in the majority of the solvents used, it can be preferable for the reaction according to the invention using barium hydroxide to be carried out in the presence of the corresponding acid of the anion $[A]^{n-}$ which is to be introduced into the ionic liquid. Particular preference is in this case given to using 1 equivalent of the corresponding acid, so that a more readily soluble mixed barium salt is initially formed, and this is subsequently reacted with the ionic liquid to be modified.

When barium hydroxide or mixed barium salts are used, the ionic liquid can be reacted by adding it to a solution of barium hydroxide or the mixed barium salt. As an alternative, it is also possible to place the barium hydroxide or the mixed barium salt in a reaction vessel and add the ionic liquid to be modified, if appropriate as a solution in water and/or one of the above-described conventional solvents.

In the first process step, the reaction of the ionic liquid to be modified with the alkoxide or with the barium hydroxide may form a sparingly soluble precipitate, for example of alkali metal halides or alkaline earth metal halides, when using alkoxides of these metals and ionic liquids containing halide ions, or of barium sulfate when using barium hydroxide and ionic liquids containing sulfate ions or hydrogensulfate anions. For this reason, the precipitated solid is separated off if necessary after the first process step.

The ionic liquid $[Q^+]_n[X^-]^{n-}$ obtained in the first process step can, if appropriate, be isolated before the second process step.

In the second process step of the process of the invention, the strongly basic ionic liquid obtained is neutralized with an acid $[H^+]_n[A]^{n-}$. Acids suitable for this purpose have a $pK_S$ which is lower than that of the corresponding acids of the anion $[X]^{n-}$.

Possible acids for this purpose are Brönsted and Lewis acids. The definitions of Brönsted and Lewis acids are given in Hollemann-Wiberg, Lehrbuch der Anorganischen Chemie, 91st-100th Edition, Walter de Gruyter, Berlin New York 1985, p. 235 and p. 239. Lewis acids for the purposes of the present invention also include the Lewis acids used as Friedel-Crafts catalysts as described in George A. Olah, Friedel-Crafts and Related Reactions, Vol. I, 191 to 197, 201 and 284-90 (1963). Examples which may be mentioned are aluminum trichloride ($AlCl_3$), iron(III) chloride ($FeCl_3$), aluminum tribromide ($AlBr_3$) and zinc chloride ($ZnCl_2$).

In general, the Lewis acids to be used according to the invention contain cationic forms of the metals of groups Ib, IIb, IIIa, IIIb, IVa, IVb, Va, Vb, VIIb, VIIb and VIII of the Periodic Table of the Elements and the rare earths, for example lanthanum, cerium, praseodymium, neodymium, samarium, europium, gadolinium, terbium, dysprosium, holmium, erbium, thulium, ytterbium or lutetium.

Particular mention may be made of zinc, cadmium, beryllium, boron, aluminum, gallium, indium, thallium, titanium, zirconium, hafnium, erbium, germanium, tin, vanadium, niobium, scandium, yttrium, chromium, molybdenum, tungsten, manganese, rhenium, palladium, thorium, iron, copper and cobalt. Preference is given to boron, zinc, cadmium, titanium, tin, iron, cobalt.

Possible counterions of the Lewis acid are $F^-$, $Cl^-$, $Cl^-$, $ClO_3^-$, $ClO_4^-$, $Br^-$, $I^-$, $IO_3^-$, $CN^-$, $OCN^-$, $SCN^-$, $NO_2^-$, $NO_3^-$, $HCO_3^-$, $HCO_3^-$, $CO_3^{2-}$, $S^{2-}$, $SH^-$, $HSO_3^-$, $SO_3^{2-}$, $HSO_4^-$, $SO_4^{2-}$, $S_2O_2^{2-}$, $S_2O_4^{2-}$, $S_2O_5^{2-}$, $S_2O_6^{2-}$, $S_2O_7^{2-}$, $S_2O_8^{2-}$, $H_2PO_2^-$, $H_2PO_4^-$, $HPO_4^{2-}$, $PO_4^{3-}$, $P_2O_7^{4-}$, dithiocarbamate, salicylate, $(OC_nH2_{n+1})^-$, $(C_nH_{2n-1}O_2)^-$, $(C_nH_{2n-3}O_2)^-$ and $(C_{n+1}H_{2n-2}O_4)^{2-}$, where n is from 1 to 20, methanesulfonate ($CH_3SO_3^-$), trifluoromethanesulfonate ($CF_3SO_3^-$), toluenesulfonate ($CH_3C_6H_4SO_3^-$), benzenesulfonate ($C_6H_5SO_3^-$), hydroxide ($OH^-$), anions of aromatic acids such as benzoic acid, phthalic acid and the like and 1,3-dicarbonyl compounds.

Mention may also be made of carboxylates, in particular formate, acetate, trifluoroacetate, propionate, hexanoate and 2-ethylhexanoate, stearate and oxalate, acetylacetonate, tartrate, acrylate and methacrylate, preferably formate, acetate, propionate, oxalate, acetylacetonate, acrylate and methacrylate.

Further possible Lewis acids are boron-containing compounds of the general formula $BR'_n(OR'')_m$ where n=0, 1, 2, 3 and m=3−n, where R' and R'' are each, independently of one another, hydrogen, $C_1$-$C_{18}$-alkyl, $C_6$-$C_{12}$-aryl, $C_5$-$C_{12}$-cycloalkyl, $C_2$-$C_{18}$-alkyl which may be interrupted by one or more oxygen and/or sulfur atoms and/or one or more substituted or unsubstituted imino groups, or a five- to six-membered, oxygen-, nitrogen- and/or sulfur-containing heterocycle or two of them together form an unsaturated, saturated or aromatic ring which may be interrupted by one or more oxygen and/or sulfur atoms and/or one or more substituted or unsubstituted imino groups, where the radicals mentioned may each be substituted by functional groups, aryl, alkyl, aryloxy, alkyloxy, halogen, heteroatoms and/or heterocycles. The radicals R' can also be joined to one another.

Apart from the abovementioned $AlCl_3$, $FeCl_3$, $AlBr_3$ and $ZnCl_2$, preferred examples of Lewis acids are $BeCl_2$, $ZnBr_2$, $ZnI_2$, $ZnSO_4$, $CuCl_2$, $CuCl$, $Cu(O_3SCF_3)_2$, $CoCl_2$, $CoI_2$, $FeI_2$, $FeCl_2$, $FeCl_2(THF)_2$, $TiCl_4(THF)_2$, $TiCl_4$, $TiCl_3$, $ClTi(OiPr)_3$, $SnCl_2$, $SnCl_4$, $Sn(SO_4)$, $Sn(SO_4)_2$, $MnCl_2$, $MnBr_2$, $ScCl_3$, $BPh_3$, $BCl_3$, $BBr_3$, $BF_3.OEt_2$, $BF_3.OMe_2$, $BF_3.MeOH$, $BF_3.CH_3COOH$, $BF_3.CH_3CN$, $B(CF_3COO)_3$, $B(OEt)_3$, $B(OMe)_3$, $B(O/Pr)_3$, $PhB(OH)_2$, $PhB(OR)_2$ (where R=H, alkyl), 3-MeO-$PhB(OH)_2$, 4-MeO-$PhB(OH)_2$, 3-F-PhB($OH)_2$, 4-F-$PhB(OH)_2$, $(C_2H_5)_3Al$, $(C_2H_5)_2AlCl$, $(C_2H_5)AlCl_2$, $(C_8H_{17})AlCl_2$, $(C_8H_{17})_2AlCl$, $(iso-C_4H_9)_2AlCl$, $Ph_2AlCl$, $PhAlCl_2$, $Al(acac)_3$, $Al(O/Pr)_3$, $Al(OnBu)_3$, $Al(OsecBu)_3$, $Al(OE)_3$, $GaCl_3$, $ReCl_5$, $ZrCl_4$, $NbCl_5$, $VCl_3$, $CrCl_2$, $MoCl_5$, $YCl_3$, $CdCl_2$, $CdBr_2$, $SbCl_3$, $SbCl_5$, $BiCl_3$, $ZrCl_4$, $UCl_4$, $LaCl_3$, $CeCl_3$, $Er(O_3SCF_3)$, $Yb(O_2CCF_3)_3$, $SmCl_3$, $SmI_2$, $B(C_6H_5)_3$ and $TaCl_5$.

The Lewis acids can also be stabilized by alkali metal halides or alkaline earth metal halides, for example LiCl or NaCl. For this purpose, the alkali metal halides or alkaline earth metal halides are mixed with the Lewis acid in a molar ratio of 0-100:1.

Further suitable acids are, for example, hydrogen iodide (HI), hydrogen fluoride (HF), hydrogen chloride (HCl), nitric acid ($HNO_3$), nitrous acid ($HNO_2$), hydrobromic acid (HBr), carbonic acid ($H_2CO_3$), methylcarbonic acid (HO(CO)$OCH_3$), ethylcarbonic acid (HO(CO)$OC_2H_5$), n-butylcarbonic acid, sulfuric acid ($H_2SO_4^-$), hydrogensulfate ($HSO_4^-$), methylsulfuric acid (HO($SO_2$)$OCH_3$), ethylsulfuric acid (HO($SO_2$)$OC_2H_5$), phosphoric acid ($H_3PO_4$), dihydrogenphosphate ($H_2PO_4^-$), formic acid (HCOOH), acetic acid ($CH_3COOH$), propionic acid, n-butyric acid and isobutyric acid, pivalic acid, paratoluenesulfonic acid, benzenesulfonic acid, benzoic acid, 2,4,6-trimethylbenzoic acid, mandelic acid, methanesulfonic acid and trifluoromethanesulfonic acid.

Further suitable acids can be derived from the following anions $[A]^{n-}$ selected from the group consisting of the halides, halogen-containing compounds and pseudohalides of the formula:

$Br^-$, $BF_4^-$, $PF_6^-$, $AlCl_4^-$, $Al_2Cl_7^-$, $FeCl_4^-$, $BCl_4^-$, $SbF_6^-$, $AsF_6^-$, $ZnCl_3^-$, $SnCl_3^-$, $CF_3SO_3^-$, $(CF_3SO_3)_2N^-$, $CF_3CO_2^-$, $CCl_3CO_2^-$, $CN^-$, $SCN^-$, $OCN^-$ the sulfates, sulfites and sulfonates of the general formula:

$$SO_4^{2-}, HSO_4^-, SO_3^{2-}, HSO_3^-, R^aOSO_3^-, R^aSO_3^-$$

the phosphates of the general formula $$PO_4^{3-}, HPO_4^{2-}, H_2PO_4^-, R^aPO_4^{2-}, HR^aPO_4^-, R^aR^bPO_4^-$$

the phosphonates and phosphinates of the general formula $$R^aHPO_3^-, R^aR^bPO_2^-, R^aR^bPO_3^-$$

the phosphates of the general formula $PO_4^{3-}$, $HPO_4^{2-}$, $H_2PO_4^{-}$, $R^aPO_3^{2-}$, $R^aHPO_3^{-}$, $R^aR^bPO_3^{-}$ the phosphonites and phosphinites of the general formula $R^aR^bPO_2^{-}$, $R^aHPO_3^{-}$, $R^aR^bPO_3^{-}$, $R^aHPO^{-}$ the carboxylic acids of the general formula $R^aCOO^{-}$ the borates of the general formula $BO_3^{3-}$, $HBO_3^{2-}$, $H_2BO_3^{-}$, $R^aR^bBO_3^{-}$, $R^aHBO_3^{-}$, $R^aBO_3^{2-}$, $[BR^aR^bR^cR^d]^{-}$ den boronates of the general formula $R^aBO_2^{2-}$, $R^aR^bBO^{-}$ the carbonates and carbonic esters of the general formula $HCO_3^{-}$, $CO_3^{2-}$, $R^aCO_3^{-}$ the silicates and silicic esters of the general formula $SiO_4^{4-}$, $HSiO_4^{3-}$, $H_2SiO_4^{2-}$, $H_3SiO_4^{-}$, $R^aSiO_4^{3-}$, $R^aR^bSiO_4^{2-}$, $R^aR^bR^cSiO_4^{2-}$, $HR^aSiO_4^{2-}$, $H_2R^aSiO_4^{-}$, $HR^aR^bSiO_4^{-}$ the alkylsilane and arylsilane salts of the general formula $R^aSiO_3^{3-}$, $R^aR^bSiO_2^{2-}$, $R^aR^bR^cSiO^{-}$, $R^aR^bR^cSiO_3^{-}$, $R^aR^bR^cSiO_2^{-}$, $R^aR^b-SiO_3^{2-}$ the carboximides, bis(sulfonyl)imides and sulfonylimides of the general formula

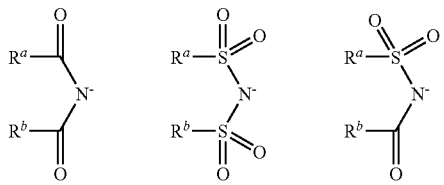

the alkoxides and aryloxides of the general formula $R^aO^{-}$ complex metal ions such as $Fe(CN)_6^{3-}$, $Fe(CN)_6^{4-}$, $MnO_4^{-}$, $Fe(CO)_4^{-}$ nitrite; nitrate, dicyanamide, where the radicals $R^a$, $R^b$, $R^c$ are each, independently of one another, $C_1$-$C_{18}$-alkyl, $C_6$-$C_{12}$-aryl, $C_5$-$C_{12}$-cycloalkyl, $C_2$-$C_{18}$-alkyl which may be interrupted by one or more non-adjacent oxygen and/or sulfur atoms and/or one or more substituted or unsubstituted imino groups or a five- to six-membered, oxygen-, nitrogen- and/or sulfur-containing heterocycle or two of them together form an unsaturated, saturated or aromatic ring which may be interrupted by one or more oxygen and/or sulfur atoms and/or one or more substituted or unsubstituted imino groups, where the radicals mentioned may each be substituted by functional groups, aryl, alkyl, aryloxy, alkyloxy, halogen, heteroatoms and/or heterocycles.

Further suitable acids can be derived from the following anions $[A]^{n-}$ selected from the group consisting of tetrasubstituted borate of the general formula $[BR^dR^eR^fR^g]^{-}$, where $R^d$ to $R^g$ are each, independently of one another, fluorine or a carbon-containing organic, saturated or unsaturated, acyclic or cyclic, aliphatic, aromatic or araliphatic radical which has from 1 to 30 carbon atoms and may contain one or more heteroatoms and/or be substituted by one or more functional groups or halogen;

(fluoroalkyl)fluorophosphate of the general formula $[PF_x(C_yF_{2y+1-z}H_z)_{6-x}]^{-}$, where $1 \leq x \leq 6$, $1 \leq y \leq 8$ and $0 \leq z \leq 2y+1$;

methide of the general formula

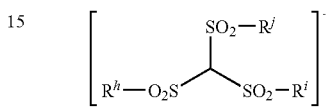

where $R^h$ to $R^j$ are each, independently of one another, hydrogen or a carbon-containing organic, saturated or unsaturated, acyclic or cyclic, aliphatic, aromatic or araliphatic radical which has from 1 to 30 carbon atoms and can contain one or more heteroatoms and/or be substituted by one or more functional groups or halogen;

imide anions —CO—N⁻—CO—, sulfonamide anions —SO₂—N⁻SO₂— and mixed carbosulfoimide anions —SO₂—N⁻—CO—.

The charge "n–" of the anion $[A]^{n-}$ is "1-", "2-" or "3-". Examples of doubly negatively charged anions are sulfate, hydrogenphosphate and carbonate. An example of a triply negatively charged anion is phosphate.

The acid can be added to the ionic liquid $[Q^+]_n[X]^{n-}$ stoichiometrically or titrimetrically to a pH which corresponds to the equivalence point of the corresponding acid-base pair. However, in further embodiments, the acid can also be used in excess or in a deficiency. Thus, the amount of acid can be from 0.5 to 1.5 equivalents, preferably from 0.8 to 1.2 equivalents, particularly preferably from 0.9 to 1.1 equivalents, in particular 1.0 equivalent, in each case based on the ionic liquid $[Q^+]_n[X]^{n-}$.

If the ionic liquid to be modified in the process of the invention is reacted with an alkoxide, the corresponding alcohol is formed in the neutralization. In a preferred embodiment of the process of the invention, the alcohol formed in the neutralization when alkoxides are used is therefore removed by distillation after the neutralization.

The neutralization in the second process step takes place at temperatures of preferably from –10 to 100° C., particularly preferably from 0 to 90° C., in particular from 10 to 60° C. The reaction time is preferably from 1 to 16 hours, particularly preferably from 30 minutes to 3 hours, in particular from 10 minutes to 2 hours.

The first and/or second process step(s) of the process of the invention can, if appropriate, be carried out under protective gas, for example nitrogen, noble gases or carbon dioxide.

The process of the invention can be carried out continuously or batchwise.

The process of the invention can be carried out in any suitable apparatus known to those skilled in the art. Suitable apparatuses are, for example, customary apparatuses as are described, for example, in: Kirk-Othmer, Encyclopedia of Chemical Technology, 4th Ed., Vol. 20, John Wiley & Son's, New York 1996, pages 1040 to 1055, e.g. stirred tank reactors, loop reactors, gas recycle reactors, bubble column reactors or tube reactors, each of which may, if appropriate, be provided with facilities for removing the heat of reaction. The reaction can also be carried out in a plurality, for example two or three, of the apparatuses mentioned above.

For the purposes of the present invention, the term functional group refers to groups which can be bound to a carbon atom or a heteroatom. Examples which may be mentioned are —OH (hydroxy), =O (in particular as a carbonyl group), —NH$_2$ (amino), =NH (imino), —COOH (carboxy), —CONH$_2$ (carboxamide) and —CN (cyano). Functional groups and heteroatoms can also be directly adjacent, so that combinations of a plurality of adjacent atoms such as —O— (ether), —S— (thioether), —COO— (ester), —CONH— (secondary amide) or —CONR— (tertiary amide) are also encompassed.

The process of the invention is suitable, for example, for preparing ionic liquids of the general formula [Q$^+$][BR'$_n$(OR")$_m^-$] where n=1, 2, 3 and m=4−n.

Ionic liquids of the general formula [Q$^+$][BR'$_n$(OR")$_m^-$] where n=1, 2, 3 and m=4−n are likewise provided by the present invention. Here, R' and R" are each, independently of one another, hydrogen, C$_1$-C$_{18}$-alkyl, C$_6$-C$_{12}$-aryl, C$_5$-C$_{12}$-cycloalkyl, C$_2$-C$_{18}$-alkyl which may be interrupted by one or more oxygen and/or sulfur atoms and/or one or more substituted or unsubstituted imino groups, or a five- or six-membered, oxygen-, nitrogen- and/or sulfur-containing heterocycle or two of them together form an unsaturated, saturated or aromatic ring which may be interrupted by one or more oxygen and/or sulfur atoms and/or one or more substituted or unsubstituted imino groups, where the radicals mentioned may each be substituted by functional groups, aryl, alkyl, aryloxy, alkyloxy, halogen, heteroatoms and/or heterocycles. The radicals R' can also be joined to one another.

The cation [Q$^+$] preferably has one of the above-defined structures for cations.

The cation [Q$^+$] is particularly preferably an N,N-dialkylimidazolium cation.

In a preferred embodiment, the ionic liquid of the general formula [Q$^+$][BR$_n$(OR")$_m^-$] contains the anion [BPh$_3$OR'] in which R' has one of the abovementioned meanings.

In a further, preferred embodiment, the ionic liquid [Q$^+$][BR'$_n$(OR")$_m^-$] contains the anion [BPh$_3$OR'] and an N,N-dialkylimidazolium cation as cation.

For the purposes of the present invention,

C$_1$-C$_{18}$-alkyl which may be substituted by functional groups, aryl, alkyl, aryloxy, alkyloxy, halogen, heteroatoms and/or heterocycles is, for example, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hexadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxy-ethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, and C$_2$-C$_{18}$-alkyl which may be interrupted by one or more oxygen and/or sulfur atoms and/or one or more substituted or unsubstituted imino groups is, for example, 5-hydroxy-3-oxapentyl, 8-hydroxy-3,6-dioxaoctyl, 11-hydroxy-3,6,9-trioxaundecyl, 7-hydroxy-4-oxaheptyl, 11-hydroxy-4,8-dioxaundecyl, 15-hydroxy-4,8,12-trioxapentadecyl, 9-hydroxy-5-oxanonyl, 14-hydroxy-5,10-oxatetradecyl, 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5,10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-oxatetradecyl.

If two radicals form a ring, these radicals can together be 1,3-propylene, 1,4-butylene, 2-oxa-1,3-propylene, 1-oxa-1,3-propylene, 2-oxa-1,3-propylene, 1-oxa-1,3-propenylene, 1-aza-1,3-propenylene, 1-C$_1$-C$_4$-alkyl-1-aza-1,3-propenylene, 1,4-buta-1,3-dienylene, 1-aza-1,4-buta-1,3-dienylene or 2-aza-1,4-buta-1,3-dienylene.

The number of oxygen and/or sulfur atoms and/or imino groups is not subject to any restrictions. In general, there are no more than 5 such atoms or groups in the radical, preferably not more than 4 and very particularly preferably not more than 3.

Furthermore, there is generally at least one carbon atom between two heteroatoms, preferably at least two carbon atoms between two heteroatoms.

Substituted and unsubstituted imino groups can be, for example, imino, methylimino, isopropylimino, n-butylimino or tert-butylimino.

Furthermore functional groups are carboxy, carboxamide, hydroxy, di(C$_1$-C$_4$-alkyl)amino, C$_1$-C$_4$-alkyloxycarbonyl, cyano or C$_1$-C$_4$-alkyloxy, C$_6$-C$_{12}$-aryl which may be substituted by functional groups, aryl, alkyl, aryloxy, alkyloxy, halogen, heteroatoms and/or heterocycles is, for example, phenyl, tolyl, xylyl, α-naphthyl, α-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl, C$_5$-C$_{12}$-cycloalkyl which may be substituted by functional groups, aryl, alkyl, aryloxy, alkyloxy, halogen, heteroatoms and/or heterocycles is, for example, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl or a saturated or unsaturated bicyclic system such as norbornyl or norbornenyl, a five- or six-membered, oxygen-, nitrogen- and/or sulfur-containing heterocycle, for example, furyl, thiophenyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluoropyridyl, methylthiophenyl, isopropylthiophenyl or tertbutylthiophenyl and $C_1$-$C_4$-alkyl, for example, methyl, ethyl, propyl, isopropyl, n-butyl, sec-butyl or tert-butyl.

Preference is given to R, $R^1$, $R^2$, $R^3$, $R^4$, $R^5$, $R^6$, $R^7$, $R^8$ and $R^9$ each being, independently of one another, hydrogen, methyl, ethyl, n-butyl, 2-hydroxyethyl, 2-cyanoethyl, 2-(methoxycarbonyl)ethyl, 2-(ethoxycarbonyl)ethyl, 2-(n-butoxycarbonyl)ethyl, benzyl, acetyl, dimethylamino, diethylamino and chlorine.

For the purposes of the present invention, heteroatoms can in principle be all heteroatoms which are able to formally replace a —$CH_2$—, —CH=, C≡ or =C= group. If the carbon-containing radical contains heteroatoms, preference is given to oxygen, nitrogen, sulfur, phosphorus and silicon. Preferred groups are, in particular, —O—, —S—, —SO—, —$SO_2$—, —NR—, —N=, —PR—, —$PR_2$ and —$SiR_2$—, where the radicals R are each the remaining part of the carbon-containing radical.

The present invention also provides solutions which comprise at least one ionic liquid and are obtained by the above-described process.

The present invention further provides solutions which comprise at least one ionic liquid of the general formula (II)

$[Q^+]_n[X]^{n-}$ (II)

where $[X]^{n-}$=$OH^-$, $OR^-$ where R=$C_1$-$C_{18}$-alkyl, $C_6$-alkyl, $C_5$-$C_{12}$-cycloalkyl, $HCO_3^-$, $CO_3^{2-}$, and are obtained by reacting an ionic liquid containing a phosphonium and/or ammonium cation as cation and an anion selected from the group consisting of halides, arylsulfonates, alkylsulfonates, sulfate, hydrogensulfate, alkylsulfates, hydrogencarbonate, carbonate, triflates and carboxylates with an alkoxide or a hydroxide.

The present invention also provides a process for the universal preparation of ionic liquids by introduction of virtually any anion. Here, an alkoxide or hydroxide of an ionic liquid is prepared first and this can subsequently be protinated by means of virtually any acid and in this way provided with an anion. The process of the invention is suitable for preparing a large number of different ionic liquids. In contrast to the processes known hitherto, the process of the invention is inexpensive to carry out.

The present invention is illustrated by the following examples.

EXAMPLES

EMIM=Ethylmethylimidazolium

BMIM=Butylmethylimidazolium

I. Experiments According to the Invention (Alkoxide Method)

1. Preparation of EMIM Acetate 92.6 g (0.825 mol) of potassium tert-butoxide are dissolved in 1000 ml of n-butanol at 60° C. The solution is subsequently cooled to RT and 120.9 g (0.825 mol) of molten EMIM chloride (m.p. about 85° C.) are allowed to flow into the solution. A precipitate of KCl is immediately formed. The reaction mixture is stirred for another 3 hours at RT and then filtered. The precipitate is washed with n-butanol. This gives 747.2 g of filtrate which is strongly alkaline (pH 14). A sample of the filtrate is titrated against 0.5 M HCl. According to this, 0.666 mol of EMIM tert-butoxide is present in the filtrate. To neutralize the EMIM tert-butoxide, the stoichiometric amount=49.5 g (0.825 mol) of glacial acetic acid is then added to the filtrate. The solvents are removed under reduced pressure. The oil which remains is extracted with ethyl acetate to remove traces of any excess acetic acid and is dried at 70° C. in a high vacuum. This gives 133.7 g (0.785 mol) of EMIM acetate. The yield is 95.2%. The chloride content is 0.52%, the water content is 0.04%.

2. Preparation of EMIM Tosylate 185.2 g (1.65 mol) of potassium tert-butoxide are dissolved in 2000 ml of n-butanol at 60° C. 242.0 g (1.65 mol) of molten EMIM chloride (m.p. about 85° C.) are subsequently allowed to flow into the solution. A precipitate of KCl is immediately formed. The reaction mixture is stirred for another 30 minutes at 60° C. and then filtered. The precipitate is washed with n-butanol. To neutralize the EMIM tert-butoxide, p-toluenesulfonic acid is then added to the filtrate. The solvents are removed under reduced pressure. The 1H NMR spectrum of the oil which remains shows that it comprises EMIM tosylate together with 25% of excess p-toluenesulfonic acid and also n-butanol and tert-butanol.

3. Preparation of EMIM Acetate

A reaction vessel is initially charged at RT with 119.6 (0.3 mol) of EMIM Cl as a 36.8% strength solution in ethanol. 97.1 g (0.3 mol) of a 21% strength sodium ethoxide solution are allowed to flow into this solution. A precipitate of NaCl is immediately formed. The reaction mixture is stirred for another 30 minutes at RT and then filtered. The precipitate is washed with ethanol. This gives 183.5 g of filtrate which is strongly alkaline (pH 14). A sample of the filtrate is titrated against 0.5 M HCl. According to this, 0.271 mol of EMIM ethoxide is present in the filtrate. To neutralize the EMIM ethoxide, the stoichiometric amount=16.26 g (0.271 mol) of glacial acetic acid is then added to the filtrate. The solvents are removed under reduced pressure. The oil which remains is extracted with ethyl acetate to remove traces of any excess acetic acid and is dried at 50° C. in a high vacuum. This gives 41.3 g (0.24 mol) of EMIM acetate. The yield based on the EMIM ethoxide is 90%. The chloride content is 5.6%, and the water content is 0.29%.

4. Preparation of BMIM Acetate 53.9 g (0.309 mol) of BMIM chloride are added to 100.0 g (0.309 mol) of 21% strength sodium ethoxide solution at 60° C. A precipitate of NaCl is immediately formed. The reaction mixture is stirred for another 2 hours at 60° C. and then filtered. The precipitate is washed with ethanol. This gives 268.3 g of filtrate which is strongly alkaline (pH 14). A sample of the filtrate is titrated against 0.5 M HCl. According to this, 0.2233 mol of BMIM ethoxide is present in the filtrate. To neutralize the BMIM ethoxide, the stoichiometric amount=13.2 g (0.22 mol) of glacial acetic acid is added to the filtrate. The solvents are removed under reduced pressure. The oil which remains is extracted with ethyl acetate to remove traces of any excess acetic acid and is dried at 50° C. in a high vacuum. This gives 41.9 g (0.21 mol) of EMIM acetate. The yield based on the BMIM ethoxide is 95%. The chloride content is 0.59.

5. Preparation of an Ionic Liquid by Reaction of a Basic Ionic Liquid with a Lewis Acid 9 g (0.08 mol) of potassium tert-butoxide are dissolved in 100 ml of n-butanol at 60° C. After cooling to RT, 11.7 g (0.08 mol) of EMIM Cl are added as a melt. The mixtures is stirred for another 3 hours at RT and the precipitated KCl is then filtered off and rinsed with n-butanol. This gives 97.9 g of mother liquor which, according to titration against 0.5 M HCl, contains 0.076 mol of butoxide, corresponding to a yield in this step of 95%. 18.5 g (0.076 mol) of triphenylboron are dissolved in 100 ml of n-butoxide. The 97.9 g of the butanolic solution of EMIM butoxide are subsequently added dropwise to the solution of triphenylboron. An exothermic reaction is observed. After the addition is complete, the solvent is removed under reduced pressure. This leaves 30.8 g of ionic liquid, corresponding to a yield of 95%. According to $^1$H NMR, the ionic liquid is EMIM triphenyl-n-butoxyborate. The tert-butoxide initially used has been converted into n-butoxide in the excess n-butanol used as solvent. The $^1$H NMR spectrum (CDCl$_3$) shows the corresponding signals at 7.5 ppm (m, 6H, o-Ph-H), 7.25 ppm (1H, N—CH—N), 7.0 (m, 6H, m-Ph-H), 6.9 (m, 3H, p-Ph-H), 6.35 ppm (s, 1H, N—CH—CH—N), 6.25 ppm (s, 1H, N—CH—CH—N), 3.62 (t, 2H, OCH$_2$CH$_2$CH$_2$CH$_3$), 3.4 (q, 2H, CH$_3$CH$_2$N), 2.95 ppm (s, 3H, N—CH$_3$), 1.5 (m, 2H, OCH$_2$CH$_2$CH$_2$CH$_3$), 1.4 (m, 2H, OCH$_2$CH$_2$CH$_2$CH$_3$), 1.05 (t, 3H, CH$_3$CH$_2$N), 0.9 (t, 3H, OCH$_2$CH$_2$CH$_2$CH$_3$). In the boron NMR, the signal of a borate can be seen at about −0.5 ppm. There is thus no longer any free triphenylboron, whose signal would be located at 67 ppm, present. The ionic liquid has a melting point of 99° C., and after recrystallization from ethyl acetate 105° C.

II. Experiments According to the Invention (Barium Method)

1. Preparation of EMIM Acetate 220.8 g (0.72 mol; still contains excess H$_2$SO$_4$) of EMIM HSO$_4$ are dissolved in 600 ml of water. 523.8 g (1.66 mol) of BaOH$_2$*8H$_2$O are added a little at a time at RT over a period of 30 minutes. The temperature is increased to 60° C. and the mixture is stirred for another 2 hours. It is allowed to cool overnight and the precipitated BaSO$_4$ is filtered off on a suction filter using Celite as filter aid. This gives 995.4 g of filtrate which, according to titration against 0.5 M HCl, contains 0.65 mol of EMIM OH. 43.5 g (0.72 mol) of glacial acetic acid are added. Water is removed on a rotary evaporator and the oil which remains is extracted with ethyl acetate. To remove traces of water, the oil is admixed with n-butanol and this is subsequently distilled off under reduced pressure. This gives 108.3 g (0.636 mol) of EMIM acetate. The yield based on EMIM OH is 98%. The yield based on EMIM HSO$_4$ is 88%. The oil is, according to 1H NMR, the ionic liquid EMIM acetate. The chloride content is 180 ppm, the sulfur content is 160 ppm, the barium content is 650 ppm and the water content is 0.68%.

2. Preparation of EMIM Acetate 453.5 g (1.441 mol) of BaOH$_2$*8H$_2$O are suspended in 600 g of water. The suspension is heated to 80° C. The barium salt melted about 80° C. and is then present as an emulsion in water. 220.8 g (0.72 mol; contains excess H$_2$SO$_4$) of EMIM HSO$_4$ are added dropwise to the emulsion, resulting in the temperature rising to 100° C. Despite the precipitated BaSO$_4$, the suspension remains readily stirrable. After stirring for 2 hours at 80° C., the filtrate is free of sulfate (negative sulfate test). After cooling, the precipitated BaSO$_4$ is filtered off on a suction filter using Celite as filter aid. The filtrate is admixed with 43.5 g of glacial acetic acid (0.72 mol). Water is removed on a rotary evaporator. The oil which remains is extracted with ethyl acetate. Drying under reduced pressure gives 113.3 g (0.67 mol) of EMIM acetate. The yield is 92%. The chloride content is 60 ppm, and the water content is 0.67%.

3. Preparation of EMIM Acetate 403.8 g (1.28 mol) of BaOH$_2$*8H$_2$O together with 76.9 g (1.28 mol) of glacial acetic acid and 350 g of water are placed in a reaction vessel at 75° C., giving a solution. 266.5 g (1.28 mol) of EMIM HSO$_4$ are added dropwise to the solution, resulting in the temperature rising to 86° C. Despite the precipitated BaSO$_4$, the suspension remains readily stirrable. While cooling, the mixture is stirred for another 90 minutes and the precipitated BaSO$_4$ is filtered off on a suction filter using Celite as filter aid. The filtrate is evaporated on a rotary evaporator. The residue is dried by adding n-butanol and distilling it off again. The 1H NMR spectrum indicates pure EMIM acetate.

4. Preparation of EMIM Dihydrogenphosphate 237.57 g (1.0 mol; still contains excess H$_2$SO$_4$) are dissolved in 600 ml of water. 473.3 g (1.5 mol) of BaOH$_2$*8H$_2$O are added a little at a time at RT over a period of 30 minutes. The temperature is increased to 60° C. and the mixture is stirred for another 2 hours. It is allowed to cool overnight and the precipitated BaSO$_4$ is filtered off on a suction filter using Celite as filter aid and is washed with water. This gives 1320.5 g of filtrate which, according to titration against 0.5 M HCl, contains 0.93 mol of EMIM OH. 115.3 g (1.0 mol) of 85% strength phosphoric acid are added. Water is removed on a rotary evaporator. The residue (202.8 g=0.975 mol) is a white solid having a melting point of 140° C. The yield based on EMIM HSO$_4$ is 98%. The solid is, according to $^1$H NMR, EMIM dihydrogenphosphate. The chloride content is 550 ppm, and the water content is 1.4%.

5. Preparation of EMIM Saccharinate 315.5 g (1.0 mol) of BaOH$_2$*8H$_2$O and 186.9 g (1 mol) of saccharin are suspended in 1000 ml of water at 75° C. 208.2 g (1.0 mol) of EMIM HSO$_4$ are added dropwise to the mixture over a period of 30 minutes, resulting in the suspension becoming more fluid. After stirring for another 30 minutes, the filtrate was free of sulfate (negative sulfate test). The precipitated BaSO$_4$ is filtered off on a suction filter using Celite as filter aid and is washed with water. Water is removed on a rotary evaporator. The residue (after drying under reduced pressure 285 g=0.971 mol) is a solid which, according to $^1$H NMR, is EMIM saccharinate. The water content is 0.3%. The yield is 97%. The melting point of EMIM saccharinate is about 150° C.

6. Preparation of EMIM Dihydrogenborate 631 g (2.0 mol) of BaOH$_2$*8H$_2$O and 123.6 g (2 mol) of boric acid are suspended in 500 ml of water at 60° C. 416.4 g (1.0 mol) of EMIM HSO$_4$ are added dropwise to the mixture over a period of 60 minutes. To improve the stirrability, a further 500 g of water are added. The precipitated BaSO$_4$ is filtered off on a suction filter using Celite as filter aid and is washed with water. Water together with added n-butanol is removed on a rotary evaporator. The residue (after drying under reduced pressure 247.2 g=1.44 mol) is a solid which, according to $^1$H NMR, contains the EMIM cation. The yield is 72%. The melting point of EMIM dihydrogenborate is about 40° C.

7. Preparation of EMIM Cyanurate 315.5 g (1.0 mol) of BaOH$_2$*8H$_2$O and 129.1 g (1 mol) of cyanuric acid are suspended in 500 ml of water at 60° C. 208.2 g (1.0 mol) of EMIM HSO$_4$ are added dropwise to the mixture over a period of 35 minutes. After stirring for another 8 hours, the mixture is cooled. The precipitated BaSO$_4$ is filtered off on a suction filter using Celite as filter aid. Water together with added n-butanol is removed on a rotary evaporator. The residue (after drying under reduced pressure 197.5 g=0.825 mol) is a solid which, according to 1H NMR, contains the EMIM cation. The chloride content is 0.23%. The yield is 83%. The melting point of EMIM cyanurate is about 161° C.

The invention claimed is:

1. An ionic liquid of the general formula [Q$^+$][BR'$_3$(OR")]$^-$] where [Q$^+$] is 1,3-dimethylimidazolium, 1-ethyl-3-methylimidazolium, 1-methyl-3-propylimidazolium, 1-isopropyl-3-methylimidazolium, 1-methyl-3-pentylimidazolium, 1-hexyl-3-methylimidazolium, 1-heptyl-3-methylimidazolium, 1-methyl-3-octylimidazolium, 1-decyl-3-methylimidazolium, 1-methyl-3-benzylimidazolium, 1-methyl-3-(3-phenylpropyl)imidazolium, 1-(2-ethyl)hexyl-3-methylimidazolium, 1-methyl-3-nonylimidazolium, 1-methyl-3-decylimidazolium, 1,2,3-trimethylimidazolium, 1-ethyl-2,3-dimethylimidazolium, or 1-butyl-2,3-dimethylimidazolium, where R' is phenyl and R" is selected from the group consisting of hydrogen, C$_1$-C$_{18}$-alkyl, being selected from the group consisting of methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hexadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxy-ethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, C$_6$-C$_{12}$-aryl, being selected from the group consisting of phenyl, tolyl, xylyl, α-naphthyl, α-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl and ethoxymethylphenyl, C$_5$-C$_{12}$-cycloalkyl, being selected from the group consisting of cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl, norbornyl, and norbornenyl.

2. The ionic liquid according to claim 1, wherein the cation [Q$^+$] is an N,N-dialkylimidazolium cation.

3. A solution which comprises at least one ionic liquid according to claim 1.

* * * * *